(12) United States Patent
Arbiser

(10) Patent No.: US 8,809,283 B2
(45) Date of Patent: Aug. 19, 2014

(54) PROTEASOME INHIBITORS AND USES THEREOF

(75) Inventor: Jack Arbiser, Atlanta, GA (US)

(73) Assignee: Natuderm, LLC, Atlanta, GA (US)

( * ) Notice: Subject to any disclaimer, the term of this patent is extended or adjusted under 35 U.S.C. 154(b) by 1014 days.

(21) Appl. No.: 11/437,244

(22) Filed: May 19, 2006

(65) Prior Publication Data

US 2007/0004647 A1    Jan. 4, 2007

Related U.S. Application Data

(60) Provisional application No. 60/683,385, filed on May 20, 2005.

(51) Int. Cl.
| | |
|---|---|
| A01N 43/04 | (2006.01) |
| A61K 31/445 | (2006.01) |
| A01N 43/40 | (2006.01) |
| A01N 43/46 | (2006.01) |
| A61K 31/40 | (2006.01) |

(52) U.S. Cl.
USPC .............................. 514/25; 514/317; 514/424

(58) Field of Classification Search
None
See application file for complete search history.

(56) References Cited

U.S. PATENT DOCUMENTS

| | | | | |
|---|---|---|---|---|
| 5,034,412 A * | 7/1991 | Ku et al. | ........................ | 514/529 |
| 5,811,101 A * | 9/1998 | Waltman | ........................ | 424/744 |
| 5,972,993 A | 10/1999 | Ptchelintsev | | |
| 2002/0002139 A1 | 1/2002 | Hodge et al. | | |
| 2003/0105031 A1 | 6/2003 | Rosenbloom | | |
| 2003/0225356 A1 | 12/2003 | Kulichikhin et al. | | |
| 2004/0137077 A1 * | 7/2004 | Ancira et al. | ................. | 424/616 |
| 2004/0156873 A1 | 8/2004 | Gupta | | |
| 2004/0170581 A1 * | 9/2004 | Henry et al. | ..................... | 424/59 |
| 2004/0243042 A1 | 12/2004 | Lipman | | |
| 2004/0259920 A1 | 12/2004 | Zouboulis | | |
| 2011/0086907 A1 | 4/2011 | Zouboulis | | |

FOREIGN PATENT DOCUMENTS

| | | | |
|---|---|---|---|
| CA | 2530963 | A1 | 6/2006 |
| EP | 0582147 | A2 | 2/1994 |
| EP | 1674095 | A1 | 6/2006 |
| WO | 9101124 | A1 | 2/1991 |
| WO | 9811778 | A1 | 3/1998 |
| WO | 0247703 | A2 | 6/2002 |
| WO | 02087645 | A1 | 11/2002 |
| WO | 02089791 | A2 | 11/2002 |
| WO | WO 02092410 | A1 * | 11/2002 |
| WO | 03000634 | A1 | 1/2003 |

OTHER PUBLICATIONS

Greaves, M.W., et al., "Treatment of Psoiasis", provided in IDS, 1995, New England Journal of Medicine, 337(9), pp. 581-560.*
Gonzalez-Lopez et al., Br J Dermatol., May 2008; 158(5):1146-8, Epub Feb. 2008.
Yu et al., J Biol Chem, May 30, 1997; 272(22):14017-20.
Tanaka, K., J Biochem. Feb. 1998; 123(2):195-204.
Brooks et al., Biochem J. Feb. 15, 2000;346Pt 1:155-61.
Ren et al., Oncogene, Mar. 9, 2000;19(11):1419-27.
Nam et al., J Biol Chem. Apr. 20, 2001;276(16):13322-30, Epub Jan. 26, 2001.
Greaves et al., N Engl J Med. Mar. 2, 1995;332(9):581-8.
Finley et al., Annu Rev Cell Biol. 1991;7:25-69.
Arbiser et al., J Am Acad Dermatol, Jun. 1999;40(6 Pt 1):925-9.
Arbiser et al., Mol Med. Jun. 1998;4(6):376-83.
LaMontagne et al., Am J Pathol. Dec. 2000; 157(6):1937-45.
Kwon et al., Diabetes, Apr. 1998;47(4):583-91.
Mayr et al., J Biol Chem. Apr. 8, 2005;280(14):13229-40, Epub Jan. 19, 2005.
Robinson et al., Mol Pharmacol. Oct. 1996;50(4):846-55.
Zusheng et al., Medical Recapitulate 10(4):249-250.
Keller et al., Mech Ageing Dev. Jan. 24, 2000;113(1):61-70.
Rivett et al., J Pept Sci. Sep. 2000;6(9):478-88.
Tanaka et al., New Biol. Mar. 1992;4(3):173-87.
Arbiser, J., et al., "Naturally Occurring Proteasome Inhibitors from Mate Tea (Ilex paraguayensis) Serve as Models for Topical Proteasome Inhibitors", "J Invest Dermatol", Aug. 2005, pp. 207-212, vol. 125, No. 2.
International Preliminary Report on Patentability for PCT/US06/019591, Dec. 6, 2007, pp. 1-6.
Lee et al., Agric. Chem. Biotechnol. Dec. 2004;47(1):27-28.
Hanessian, S., et al., "Design and Synthesis of Functionalized Glycomers as Non-Peptidic Ligands for SH2 Binding and as Inhibitors of A-431 Human Epidermoid and HT-29 Colon Carcinoma Cell Lines", "Bioorganic and Medicinal Chemistry Letters", 2000, pp. 439-442, vol. 10.
Nazem, N., et al., "Polymer-Additive Extraction via Pressurized Fluids and Organic Solvents of Variously Cross-Linked Poly(methylmethacrylates)", "Journal of Chromatographic Science", Apr. 2002, pp. 181-186, vol. 40, No. 4.

\* cited by examiner

Primary Examiner — Michael G Hartley
Assistant Examiner — Lance Rider
(74) Attorney, Agent, or Firm — Hulquist, PLLC.; David Bradin

(57) ABSTRACT

The invention relates to methods and compositions for inhibiting proteasome activity using cinnamate compounds. These cinnamate compounds can be formulated for topical or systemic use for skin disorders such as psoriasis.

17 Claims, 9 Drawing Sheets

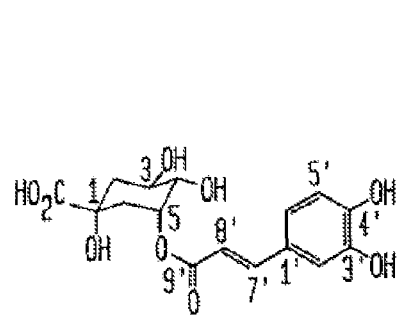
T-2: 5-CAFFEOYLQUINIC ACID (5-CQ)
"NEOCHLOROGENIC ACID"
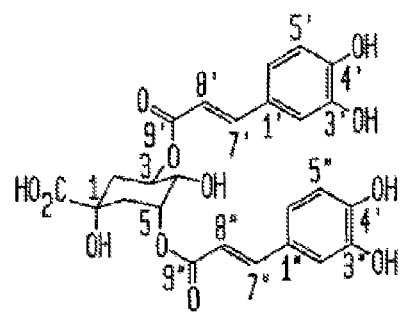
T-5: 3,5-DICAFFEOYLQUINIC ACID (3,5-DCQ)
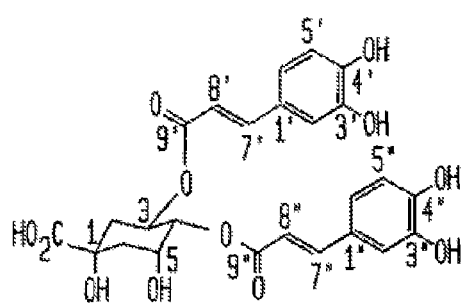
T-6: 3,4-DICAFFEOYLQUINIC ACID (3,4-DCQ)
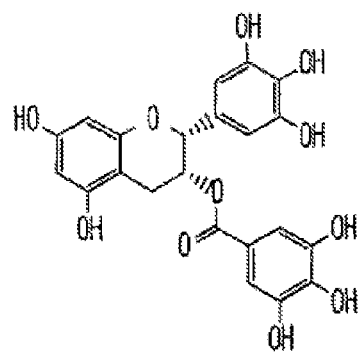
EGCG: (-)-EPIGALLOCATECHIN-3-O-GALLATE
Figure 1

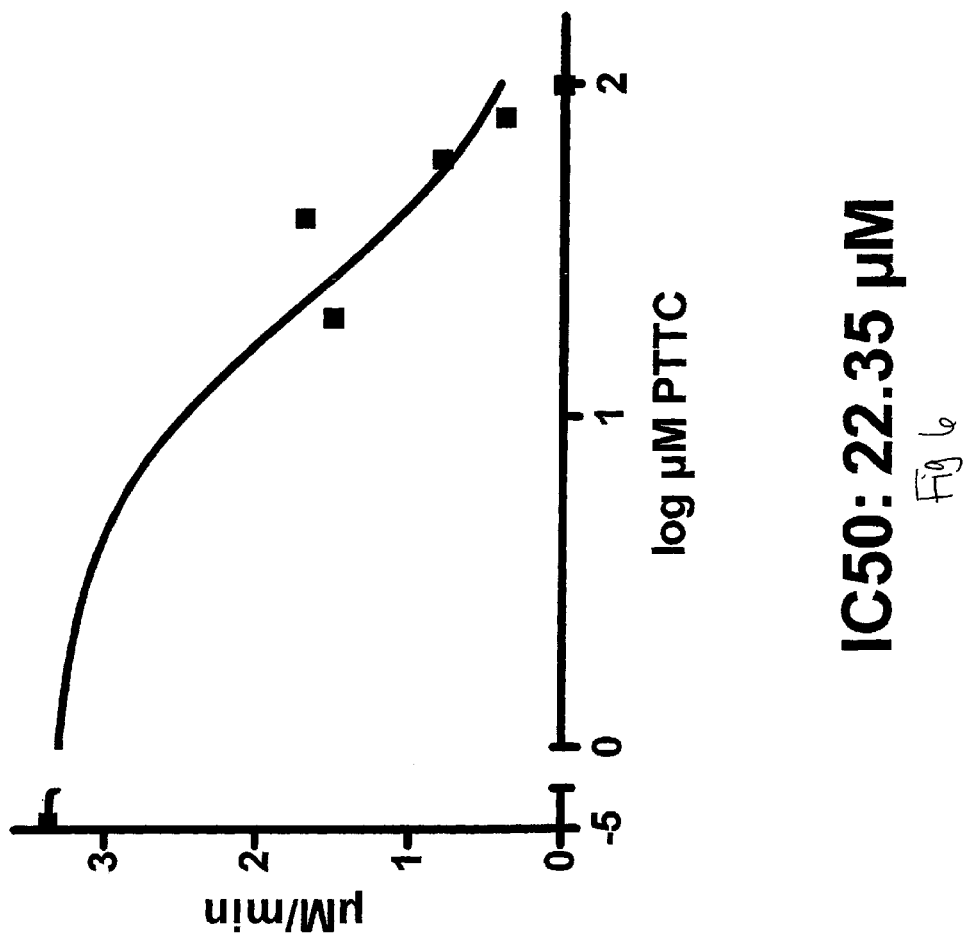

Irganox® 1076

Irganox® 1520

Irganox® 565

Irganox® 1035

Irganox® 1425

Irganox® 1330

PROTEASOME INHIBITORS AND USES THEREOF

This application claims the priority of U.S. Provisional Patent Appl. Ser. No. 60/683,385, filed May 20, 2005, the entire disclosure of which is specifically incorporated herein by reference.

FIELD OF THE INVENTION

The invention relates to treating skin disorders by proteasome modulation.

BACKGROUND OF THE INVENTION

Psoriasis is a skin disorder of unknown etiology. It is characterized by pain, itching, reduction of manual dexterity, and cosmetic problems such as prominent hand, leg, or facial lesions. Other skin conditions such as acne, seborrheic dermatitis, and skin damage caused by aging and/or photoaging, may manifest with similar symptoms and are often just as painful for their sufferers.

To date, there is no cure for psoriasis, only suppressive therapy (Greaves et al. (1995), *Drug Therapy*, 332: 581-588). Existing therapies decrease the severity and extent of psoriasis to a point at which it no longer substantially interferes with the patient's occupation, well-being, or personal or social life.

Both topical and systemic treatments for psoriasis are currently available depending on the severity of the disease. The topical treatment of psoriasis uses emollients, keratolytic agents, coal tar, anthralin, corticosteroids of medium to strong potency, and calpotriene. Systemic treatment is used in patients with physically, socially, or economically disabling psoriasis that has not responded to topical treatment. Generally, systemic treatment employs phototherapy with ultraviolet B irradiation. Alternatively, photochemotherapy can be used, which combines the photosensitizing drug methoxsalen with ultraviolet A phototherapy (PUVA), methotrexate, etretinate, systemic corticosteroids, and cyclosporine. However, these topical and systemic treatments have variable efficacy and undesired side effects. Similar treatments have also been attempted for acne, seborrheic dermatitis, and skin damage caused by aging and/or photoaging, with equally limited success.

Accordingly, a need exists for an effective skin disorder treatment that avoids the disadvantages associated with the currently available topical or systemic treatments. More specifically, an effective treatment for psoriasis, acne, seborrheic dermatitis, and skin damage caused by aging and/or photoaging is needed that does not have the same disadvantages as currently available topical or systemic treatments.

SUMMARY OF THE INVENTION

The present invention is based, in part, on the discovery that cinnamate compounds isolated from mate tea exhibit proteasome modulation activity, and in particular, proteasome inhibitory activity. These compounds can be used to topically or systemically treat disorders associated with proteasome activity. For example, the isolated cinnamate compounds can be used topically for a variety of skin disorders such as psoriasis. The cinnamate compounds can also be used systemically for those disorders associated with aberrant proteasome function such as skin disorders (e.g., psoriasis, acne, and the like), certain precancerous conditions such as myeloddysplastic conditions, as well as cancers such as leukemias, lymphomas, sarcomas, epithelial cancers, or HIV.

Accordingly, in one aspect, the invention pertains to a composition comprising an amount of a cinnamate compound effective to inhibit proteasome activity. A cinnamate compound is a three carbon carboxylic acid attached to an aromatic group. In one embodiment, the cinnamate compound has the general structure shown below as structure I,

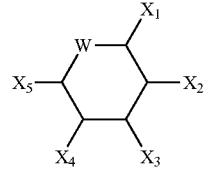

Structure I wherein W is selected from the group consisting of a methyl group, an alkyl group, a methylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, an alkyl group, an aryl group, a nitro group, a cyano group, a thiol group, a thioether group, an amino group, an amido group, and an OR group, where R is an ester of cinnamate, a dihydrocinnamate, and a hydroxyl group.

In another embodiment, the cinnamate compound has the general structure shown below as structure II,

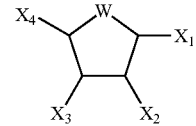

Structure II wherein W is selected from the group consisting of a methyl group, an alkyl group, a methylene group, an amine group, an acyl group, a carbonyl group, an oxygen atom, a sulfur atom, and wherein $X_1$ to $X_4$ are independently selected from the group consisting of a hydrogen atom, a halogen, a hydroxyl group, an ether group, an alkyl group, an aryl group, a nitro group, a cyano group, a thiol group, a thioether group, an amino group, an amido group, and an OR group, where R is an ester of cinnamate, a dihydrocinnamate, and a hydroxyl group.

One example of a cinnamate compound is a caffeoyl ester in which the number of esters in the caffeoyl ester can range from about 1 to 6, or about 3 to 5. The number of esters affect the activity of the cinnamate compound, such as increasing or improving the potency for inhibition of proteasome activity. Examples of caffeoyl ester include, but are not limited to, 5-caffeoylquinic acid, 3,5-dicaffeoylquinnic acid, 3, 4, dicaffeoylquinic acid and analogs or derivatives thereof.

In another aspect, the invention pertains to a composition comprising a caffeoyl ester in combination with a pharmaceutically acceptable carrier for topical administration. The caffeoyl ester is present in a dosage effective to treat a skin disorder such as psorasis, acne, rosacea, and eczema. The caffeoyl ester used in the composition can be 3,5-dicaffeoylquinnic acid and analogs or derivatives thereof, and can be present at a concentration in the range of about 0.01% to 10%.

In another aspect of the invention compounds related to aforementioned cinnamate compounds may exhibit proteasome modulation activity. In particular, the invention relates to phenolic antioxidants that can be used to modulate proteasome activity. More specifically the use of the IRGANOX® family of phenolic antioxidants produced by Ciba Specialty Chemicals are contemplated by the invention.

In yet another aspect, the invention pertains to a method of treating a disorder associated with proteasome activity by administering a composition comprising an amount of a cinnamate compound effective to inhibit proteasome activity, such that the inhibition of proteasome activity treats the disorder. The composition containing the cinnamate compound can be applied topically to treat skin disorders such as psoriasis, acne, rosacea, and eczema. Alternatively, the composition containing the cinnamate compound can be administered systemically to treat a disorder associated with aberrant proteasome activity such as skin disorders (e.g., psoriasis, acne, and the like), autoimmune disorders (e.g., lupus, arthritis, and multiple sclerosis0, precancerous conditions (e.g., myeloddysplastic conditions), cancers (e.g., bladder cancer, leukemias, lymphomas, sarcomas, epithelial cancers), human immunodeficiency virus (HIV) and transplant rejection.

BRIEF DESCRIPTION OF DRAWINGS

FIG. 1 depicts the chemical structures of proteasome inhibitors isolated from mate tea;

FIG. 6 depicts GgIP3K-A/PTTC inhibits chymotrypsin-like proteasome inhibitor.

DETAILED DESCRIPTION OF THE INVENTION

Figure 2:
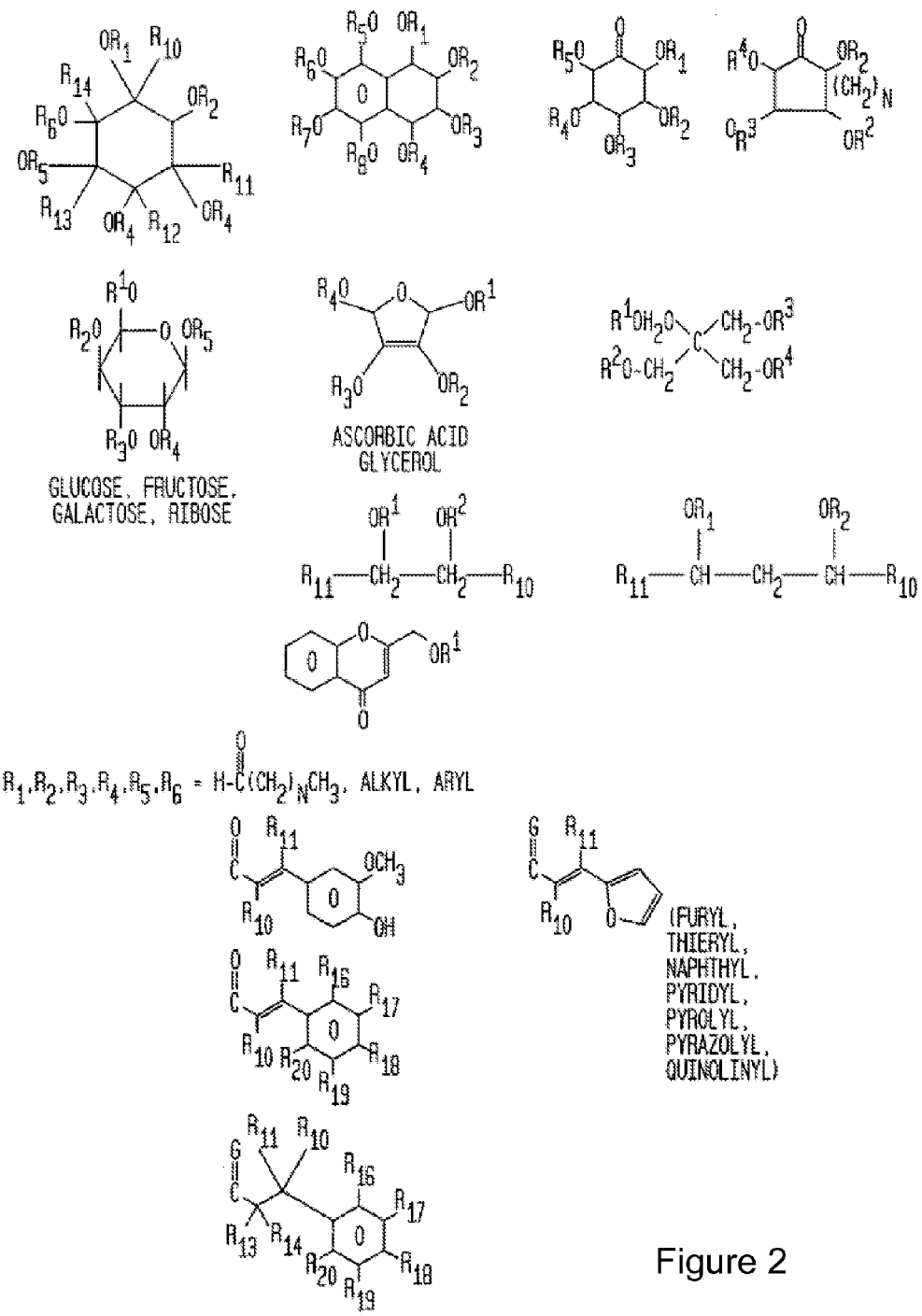
FIG. 2 depicts the derivative chemical structures of proteasome inhibitors of FIG. 1.

Certain exemplary embodiments of the invention will now be described to provide an overall understanding of the principles of the structure, function, manufacture, and use of the methods and compositions disclosed herein. Those skilled in the art will understand that the methods and compositions specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one aspect, the invention pertains to using cinnamate compounds to modulate proteasome activity. Cinnamate is a three carbon carboxylic acid attached to a 5 or 6 ring aromatic group, such as a phenyl group, a furyl group, a thienyl group, a naphthyl group, a pyridyl group, a pyrolyl group, a pyrazolyl group, and a quinolinyl group.

Plant extracts are a major source of chemopreventive, antiangiogenic, and antitumor agents. These include potent agents which are present in small quantities, as well as compounds which form a major portion of human diets. The mechanisms through which these compounds prevent the development of malignancy are not completely understood. The lack of known mechanism makes isolation and rational design of synthetic congeners difficult, as the structural features required for structure-function relationships are difficult to determine without adequate in vitro assays.

Ras-transformed endothelial cells were used as a screening tool to isolate naturally occurring compounds which may have antitumor or antiangiogenic activities, or both (Arbiser, et al., (1998) *Mol. Med.* 4, 376-383; Arbiser et al., (1999) *J. Am. Acad. Dermatol.* 40, 925-929). Using this assay, partially purified extracts were obtained from the plant Ilex paraguayensis. These extracts were chemically characterized and found to contain cinnamate compounds and in particular, caffeoyl esters of quinic acid.

A cinnamate compound isolated form mate tea is represented in structure I below

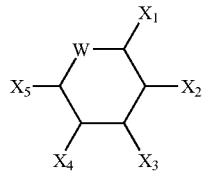

Structure I wherein W is selected from the group consisting of a methyl group, an alkyl group, a methylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, an alkyl group, an aryl group, a nitro group, a cyano group, a thiol group, a thioether group, an amino group, an amido group, and an OR group, where R is an ester of cinnamate, a dihydrocinnamate, and a hydroxyl group.

In one embodiment, the hydrogen atoms on the 3 carbon chain or aromatic ring can be replaced with a group selected from the group consisting of a halogen, hydroxyl group, ether group, alkyl group, aryl group, nitro group, cyano group, thiol group, thioester group, amino group, amido group.

Another cinnamate compound isolated from mate tea is represented in structure II below

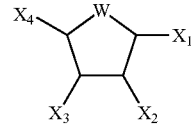

Structure II wherein W is selected from the group consisting of a methyl group, an alkyl group, a methylene group, an amine group, an acyl group, a carbonyl group, an oxygen atom, a sulfur atom, and wherein $X_1$ to $X_4$ are independently selected from the group consisting of a hydrogen atom, a halogen, a hydroxyl group, an ether group, an alkyl group, an aryl group, a nitro group, a cyano group, a thiol group, a thioether group, an amino group, an amido group, and an OR group, where R is an ester of cinnamate, a dihydrocinnamate, and a hydroxyl group.

One example of a cinnamate compound is a caffeoyl ester which comprises a hydroxy acid group. FIG. 1 shows some examples of caffeoyl esters which include, but are not limited to, 5-caffeoylquinic acid, 3,5-dicaffeoylquinnic acid, 3, 4, dicaffeoylquinic acid and analogs or derivatives thereof. Other structural analogs and derivatives of cinnamate compounds are shown in FIG. 2. These analogs and derivatives can be generated using routine chemical synthesis techniques to modify the functional groups of these structures. These modifications can be used to increase, or enhance activity of the cinnamate compound, such as increasing the inhibition potency of the compound.

In another embodiment of the invention, phenolic antioxidants structurally related to the cinnamate compounds of the invention can be used to modulate proteasome activity. One example of phenolic antioxidant compounds that are related to the cinnamate compounds of the invention is the IRGANOX® family of phenolic antioxidants produced by Ciba Specialty Chemicals. The structures of some of the IRGANOX® compounds that are contemplated by the invention are shown in FIGS. 7A-7F. These can include, but are not limited to Ciba® IRGANOX® 1010, Ciba® IRGANOX® 245 DW, Ciba® IRGANOX® 1035, Ciba® IRGANOX® 565, Ciba® IRGANOX® 1076, Ciba® IRGANOX® 1425, Ciba® IRGANOX® 1098, Ciba® IRGANOX® 1520, Ciba® IRGANOX® 1135, Ciba® IRGANOX® 1726, Ciba® IRGANOX® 1330, Ciba® IRGANOX® 5057, Ciba® IRGANOX® 245, and Ciba® IRGANOX® HP 2225. Also included are combinations of phenolic antioxidants such as Ciba® IRGANOX® B 215, Ciba® IRGANOX® B 612, Ciba® IRGANOX® B 225, and Ciba® IRGANOX® 1171.

The use of certain thiosynergistic antioxidants, such as Ciba® IRGANOX® PS 800, and Ciba® IRGANOX® PS 802, as proteasome activity modulators is also contemplated by the invention.

The compounds of the invention were found to inhibit proteasome activity. Proteasomes are large ring, or cylinder-shaped multi-component complexes common to all eukaryotic cells (Tanaka et al. (1995) *New Biol.* 4: 173-187). Proteasomes, through their protein degradation activity, have been implicated in several important cell functions, including DNA repair, cell cycle progression, signal transduction, transcription, oncogenesis, growth and atrophy of developed tissues, flow of substrates through metabolic pathways, selective elimination of abnormal proteins and antigen processing and antigen presentation (Finley et al. (1991) *Annu Rev Cell Biol* 7: 25-69). The proteasome undergoes extensive modification to suit its different function. It does so by adding and replacing the individual subunits and by restructuring. The 20S proteasome provides the proteasome with its catalytic degradation power, and is well characterized. The core of the 20S proteasome consists of two copies each of seven different α and β subunits, which are arranged in four stacked rings ($\alpha_7\beta_7\beta_7\alpha_7$).

Increasing evidence is accumulating that as a result of the normal aging process the body increasingly loses the ability to adequately degrade mutated or misfolded proteins. Oxidative stress is thought to contribute to this process of protein degradation through oxidation and nitration of intracellular proteins, which makes proteins prone to cross-linking and aggregation Such aggregated proteins are more resistant to degradation in the proteasome and may cause inhibition of proteasomal function. Decreased proteasomal activity may also be caused more directly by oxidation of the proteasome itself (Keller, et al. (2000) *Mech. Ageing Dev.* 113: 61-70). Aggregates of misfolded proteins can induce a number of changes in the proteasome that can lead to aberrant immune activation and apoptotic cell death.

Proteasomal dysfunction can play an important role in the inflammatory process through modulation of key inflammatory mediators such as Jak3 kinase and IkappaB (Kwon et al., (1998) *Diabetes*, 47: 583-91; Rivett, (2000) *J. Pept. Sci.*, 6: 478-88; Yu, et al, (1997) *J. Biol. Chem.*, 272: 14017-20).

As shown in the examples presented below, the caffeoyl ester 3,5-dicaffeoylquinic acid, was found to inhibit the chymotrypsin-like activity of a purified 20S proteasome and the 26S proteasome in Jurkat T cell extracts. Furthermore, 3,5-dicaffeoylquinic acid treatment of intact Jurkat T cells caused growth arrest in G2/M phase of the cell cycle. In contrast, the fraction identified as 5-caffeoylquinic acid (neochlorogenic acid), contains much less proteasome-inhibitory activity and fails to induce G2/M arrest in Jurkat T cells. This finding suggests that proteasome activity may depend on the number of cinnamate moieties. A cinnamate tetraester (pentaerythritol tetrakis(3,5-di-tert-butyl-4-hydroxyhydrocinnamate, PTTC), which has a high number of esters, was used as a control and found to have activity against proteasomes. Using similar experiments, the caffeoyl ester of the invention were tested and found to exhibit inhibitory action on the proteasome. In addition, the data shows that caffeoyl esters with two ester groups have a higher inhibitory activity than caffeoyl esters with one ester group. Thus, the number of esters alter the activity of the cinnamate compound, such as increasing or improving the potency for inhibition of proteasome activity. In one embodiment, the caffeoyl esters can be modified to increase number of esters to range from about 1 to 6, or 3 to 5.

The compounds of the invention can be used to treat a number of dermatological disorders such as the malignant diseases angiosarcoma, hemangioendothelioma, basal cell carcinoma, squamous cell carcinoma, malignant melanoma and Kaposi's sarcoma, and the non-malignant diseases or conditions psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis Other disorders that can be treated with the compounds of the invention include, but are not limited to, autoimmune disorders such as lupus, arthritis, multiple sclerosis, precancerous conditions such as myelodysplastic conditions, cancers such as bladder cancer, leukemias, lymphomas, sarcomas, epithelial cancers, HIV, and transplant rejection.

Pharmaceutical compositions containing the compounds of the invention can be prepared based on the specific application. Application can be topical, localized, or systemic. Any of these compositions may also include preservatives, antioxidants, antibiotics, immunosuppressants, and other biologically or pharmaceutically effective agents that do not exert a detrimental effect on the normal tissue to be treated.

Compositions for local or systemic administration will generally include an inert diluent. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In one embodiment, systemic carriers can be used. Inhibitors can be systemically administered either parenterally or enterally. The composition can be administered by means of an infusion pump, for example, of the type used for delivering insulin or chemotherapy to specific organs or tumors, by injection, or by deposition using a controlled or sustained release formulation. In a preferred systemic embodiment, drugs are administered orally, in an enteric carrier if necessary to protect the drug during passage through the stomach.

The compounds of the invention can be administered systemically by injection in a carrier such as saline or phosphate buffered saline (PBS) or orally, in the case of an inhibitor such as thalidomide, in tablet or capsule form. The tablets or capsules can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

In another embodiment, local or topical carriers can be used. The inhibitors can also be applied locally or topically, in a carrier such as saline or PBS, in an ointment or gel, in a transdermal patch or bandage, or controlled or sustained release formulation. Local administration can be by injection at the site of the injury, or by spraying topically onto the injury. The inhibitor can be absorbed into a bandage for direct application to the wound, or released from sutures or staples at the site. Incorporation of compounds into controlled or sustained release formulations is well known.

For topical application, the compounds of the invention can be combined with a carrier so that an effective dosage is delivered, based on the desired activity, at the site of application. The topical composition can be applied to the skin for treatment of diseases such as psoriasis. The carrier may be in the form of an ointment, cream, gel, paste, foam, aerosol, suppository, pad or gelled stick. A topical composition for use of an ointment or gel consists of an effective amount of angiogenesis inhibitor in an ophthalmically acceptable excipient such as buffered saline, mineral oil, vegetable oils such as corn or arachis oil, petroleum jelly, Miglyol 182, alcohol solutions, or liposomes or liposome-like products.

In one form for controlled release, the composition is administered in combination with a biocompatible polymeric implant which releases the angiogenesis inhibitor over a controlled period of time at a selected site. Examples of preferred biodegradable polymeric materials include polyanhydrides, polyorthoesters, polyglycolic acid, polylactic acid, polyethylene vinyl acetate, and copolymers and blends thereof. Examples of preferred non-biodegradable polymeric materials include ethylene vinyl acetate copolymers. These can be prepared using standard techniques as microspheres, microcapsules, tablets, disks, sheets, and fibers.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a pharmacological agent of the invention is between about 0.01 to 10%, or 1 to 5% of the composition in a carrier. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The following examples are illustrative of the principles and practice of this invention. Numerous additional embodiments within the scope and spirit of the invention will become apparent to those skilled in the art.

EXAMPLES

Example 1

Isolation and Characterization of Proteasome Inhibitors from Mate Tea

This example demonstrates the methods and materials required to isolate compounds with proteasome inhibition activity from mate tea and description of methods and assays to determine the effect of the isolated compounds.

(i) Preparation of Mate Tea Extracts

Powdered mate tea (Chimarrao Laranjeiras Puraerva, Cascavel, Brazil). Mate tea (100 g) was extracted by boiling in 500 ml water for 30 minutes. Pentaerythritol tetrakis (3,5-di-tert-butyl-4-hydroxyhydrocinnamate) (PTTC) was obtained from Aldrich Chemical Co (St Louis, Mo.). Once cool, the crude aqueous extract was first filtered through a 0.45 micron filter and further filtered to exclude materials of greater than 3000 MW.

The filtered aqueous extract was lyophilized to a dry powder, which was dissolved in distilled water and analyzed by HPLC, and 5 fractions were collected. HPLC fractions were lyophilized. Each fraction was reconstituted into 10 mg/ml solutions, and the ability to inhibit proliferation of SVR cells was tested.

(ii) Cell Proliferation Assays

SVR cells ($1 \times 10^4$) were plated for 24 hours in a 24-well plate. The media was then changed to DMEM containing purified extract at a concentration of 10 mg/ml. Cells were exposed to drug for 72 hours and were counted with a Coulter Counter (Coulter, Hialeah, Fla.) according to the method of Lamontagne et al (LaMontagne et al., (2000) *Am. J. Pathol.* 157, 1937-1945). Aqueous filtered extract of mate tea exerted a strong inhibitory effect on SVR endothelium. In order to determine the component of mate tea responsible, the aqueous extract was fractionated by HPLC, and the ability of the fractions to inhibit SVR cell proliferation was assessed. The fractions that showed the most potent inhibitory effects were fractions T-2, T-5, and T-6. The structures of T-2, T-5, and T-6 were elucidated by proton NMR and mass spectroscopy (FIG. 1). Fraction T-2 was found to be 5-caffeoylquinic acid (neochlorogenic acid), fraction T-5 was found to be 3,5-dicaffeoylquinic acid, and fraction T-6 was found to be 3,4-dicaffeoylquinic acid. The NMR spectra of the compounds are shown below.

(iii) General Spectroscopic and Spectrometric Methods

The NMR spectra were recorded in CD3OD on a Bruker DRX 400 spectrometer operating at 400 MHz for 1H and 100 MHz for $^{13}C$, running gradients and using residual solvent peaks as internal references. The HRESIMS data was acquired on a Bruker BioAPEX 30es (NCNPR, University of Mississippi).

5-Caffeoylquinic acid14 (5-CQ; T-2; neochlorogenic acid): 1H NMR (CD3OD, 400 MHz): d 7.58 (1H, d, J=15.9 Hz, H-7'), 7.05 (1H, d, J=1.2 Hz, H-2'), 6.94 (1H, dd, J=8.2, 1.5 Hz, H-6'), 6.78 (1H, d, J=8.2 Hz, H-5'), 6.31 (1H, d, J=15.9 Hz, H-8'), 5.37 (1H, br d, J=4.8 Hz, H-5), 4.18 (1H, m, H-3), 3.66 (1H, dd, J=8.6, 3.2 Hz, H-4), 2.17 (3H, m, H-6ax, H-6eq, H-2eq), 1.97 (1H, dd, J=13.2, 10.4 Hz, H-2ax); 1C NMR (CD3OD, 100 MHz): d 178.4 (C, C-7), 169.2 (C, C-9'), 149.5 (C, C-4'), 147.0 (CH, C-7'), 146.8 (C, C-3'), 128.1 (C, C-1'), 123.0 (CH, C-6'), 116.6 (CH, C-5'), 115.9 (CH, C-2'), 115.2 (CH, C-8'), 75.5 (C, C-1), 75.0 (CH, C-4), 73.2 (CH, C-5), 68.3 (CH, C-3), 41.7 (CH2, C-2), 36.8 (CH2, C-6). HRESIMS m/z 377.0807 [M+Na]+ (calcd for C16H18O9Na, 377.0843).

3,5-Dicaffeoylquinic acid14 (3,5-DCQ; T-5): 1H NMR (CD3OD, 400 MHz): d 7.62 (1H, d, J=16.0 Hz, H-7' or H-7"), 7.58 (1H, d, J=16.0 Hz, H-7' or H-7"), 7.07 (2H, br s, H-2', -2"), 6.97 (2H, m, H-6', H-6"), 6.79 (1H, d, J=8.0 Hz, H-5', H-5"), 6.35 (1H, d, J=16.0 Hz, H-8' or H-8"), 6.27 (1H, d, J=16.0 Hz, H-8' or H-8"), 5.44 (1H, m, H-3), 5.40 (1H, br d, J=5.9 Hz, H-5), 3.99 (1H, dd, J=7.4, 3.1 Hz, H-4), 2.34-2.15 (4H, m, H-2, H-6); 13C NMR (CD3OD, 100 MHz): d 177.5 (C, C-7), 168.5 (C, C-9' or C-9"), 168.3 (C, C-9' or C-9"), 149.7 (2C, C-4', C-4"), 147.4 (CH, C-7' or C-7"), 147.2 (CH, C-7' or C7"), 146.9 (2C, C-3', C-3"), 128.0 (2C, C-1', C-1"), 123.2 (CH, C-6' or C-6"), 123.1 (CH, C-6' or C-6"), 116.6 (2CH, C-5', C-5"), 115.7 (1C each, d, C-2"), 115.5 (1C each, d, C-2'), 115.4 (1C each, d, C-8"), 115.2 (1C each, d, C-8'), 74.8 (C, C-1), 72.6 (CH, C-5), 72.2 (CH, C-3), 70.7 (CH, C-4), 37.7 (CH2, C-2), 36.1 (CH2, C-6). HRESIMS m/z 539.1160 [M+Na]+ (calcd for C25H24O12Na, 539.1116).

3,4-Dicaffeoylquinic acid14 (3,4-DCQ; T-6): 1H NMR (CD3OD, 400 MHz): d 7.60 (1H, d, J=15.9 Hz, H-7' or H-7"), 7.52 (1H, d, J=15.9 Hz, H-7' or H-7"), 7.03 (1H, br s, H-2' or H-2"), 7.01 (1H, br s, H-2' or H-2"), 6.91 (2H, m, H-6', H-6"), 6.75 (1H, d, J=8.0 Hz, H-5', -5"), 6.29 (1H, d, J=15.9 Hz, H-8' or H-8"), 6.20 (1H, d, J=15.9 Hz, H-8' or H-8"), 5.64 (1H, m, H-3), 5.14 (1H, dd, J=9.0, 2.6 Hz, H-4), 4.39 (1H, m, H-5), 2.32-2.11 (4H, m, H-2, H-6); 13C NMR (CD3OD, 100 MHz): d 176.8 (C, C-7), 168.7 (C, C-9' or C-9"), 168.4 (C, C-9' or C-9"), 149.7 (2C, C-4', C-4"), 147.7 (2CH, C-7',7"), 146.8 (2C, C-3', C-3"), 127.7 (2C, C-1', C-1"), 123.3 (2CH, C-6', C-6"), 116.6 (2CH, C-5', C-5"), 115.3 (2CH, C-2', C-2"), 114.8 (2CH, C-8', C-8"), 76.3 (C, C-1), 75.8 (CH, C-4), 69.4 (CH, C-5), 69.1 (CH, C-3), 39.4 (CH2, C-2), 38.4 (CH2, C-6).

The HPLC fractions were found to be 5-caffeoylquinic acid (5-CQ; neochlorogenic acid), 3,5-dicaffeoylquinic acid (3,5-DCQ), and 3,4-dicaffeoylquinic acid (3,4-DCQ), respectively. The $^1H$ and $^{13}C$ NMR spectroscopic data for the compounds isolated by HPLC were identified as three quinic acid derivatives. The relative number of caffeoyl ester groups in each metabolite was evident from the number of characteristic ester carbonyl carbon resonances observed in the and $^{13}C$ NMR spectrum of each compound. The $^{13}C$ NMR spectrum of 5-CQ (neochlorogenic acid) contained one carbon resonance for the free carboxylic acid (178.4 ppm for C-7) and one carbon signal for the single ester carbonyl (169.2 ppm for C-9'). The di-substituted nature of the two dicaffeoylquinic acid derivatives were evident from the presence of two separate ester carbonyl resonances in the and $^{13}C$ NMR spectrum of 3,5-DCQ (168.5 for C-9', 168.3 ppm for C-9") and 3,4-DCQ (168.7 for C-9', 168.4 for C-9"). The substitution patterns of the caffeoyl ester moieties were identified, based upon the characteristic downfield chemical shifts (1 ppm or greater) of the oxygen-bearing alpha-methine proton signals in the $^1H$ NMR spectrum of each of the caffeoyl-substituted quinic acid derivatives. Since all were previously reported known compounds, a detailed structure elucidation of each metabolite was not required. In addition, the molecular composition of 5-CQ ($C_{16}H_{18}O_9$) and 3,5-DCQ ($C_{25}H_{24}O_{12}$) were confirmed by high-resolution ESIMS analysis of the sodium adducts of each compound, respectively.

Example 2

Inhibition of Purified 20S Proteasome Activity by HPLC-Purified Mate Tea Fractions This example describes the how to analyze the inhibitory effect of isolated fractions of mate tea in vitro, using purified 20S proteasome. The chymotrypsin-like activity of purified 20S proteasome was measured as previously described (Nam et al., (2001) *J. Biol. Chem.* 276, 13322-13330). Briefly, purified prokaryotic 20S proteasome (0.5 µg) was incubated with 20 µM fluorogenic peptide substrate, Suc-Leu-Leu-Val-Tyr-AMC for 30 min at 37° C. in 100 µl of assay buffer (50 mM Tris-HCl, pH 7.5), with or without a mate tea fraction at indicated concentrations. After incubation, production of hydrolyzed 7-amido-4-methyl-coumarin (AMC) groups was measured using a multi-well plate VersaFluor™ Fluorometer with an excitation filter of 380 nm and an emission filter of 460 nm (Bio-Rad).

Figure 3:
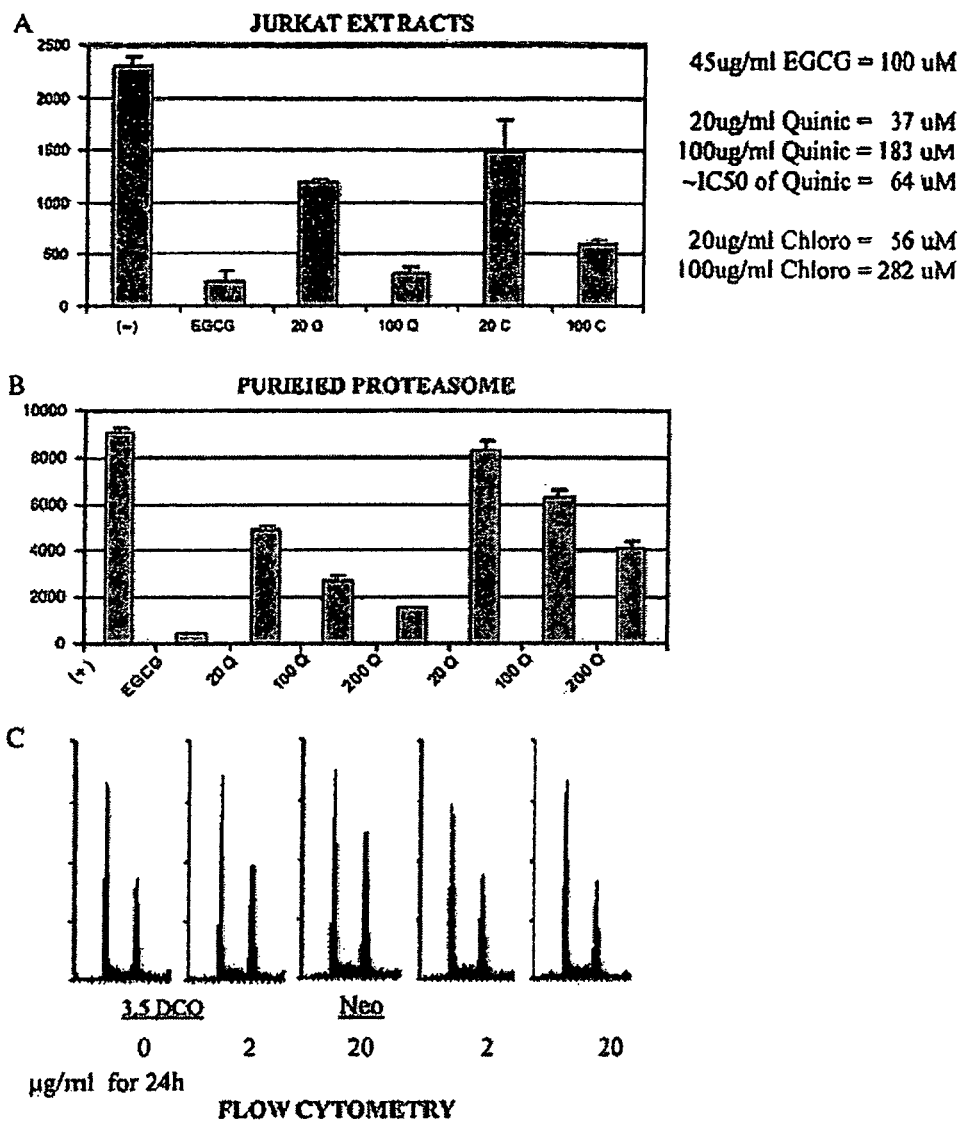
FIG. 3A depicts the effect of 3,5-dicaffeoylquinic acid on proteasome function in vitro compared with neochlorogenic acid.
FIG. 3B depicts the effect of 3,5-dicaffeoylquinic and neochlorogenic acid on proteasome function in vivo.
FIG. 3C depicts the effect of 3,5-dicaffeoylquinic acid (3,5-DCQ) on proteasome function in vitro compared with neochlorogenic acid (Neo) on cell cycle progression in Jurkat cells.
Figure 4:
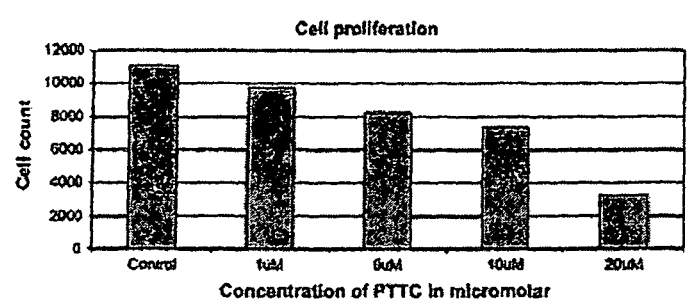
FIG. 4 depicts the effect of PTTC on proliferation of SVR cells.
Figure 5:
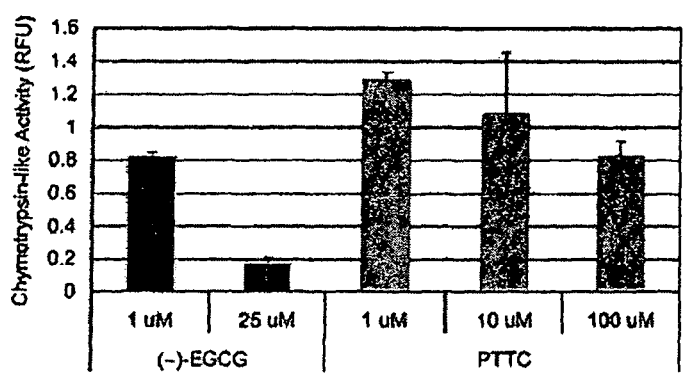
FIG. 5 depicts PTTC inhibits chymotrypsin-like proteasome inhibitor.
Figure 7A:
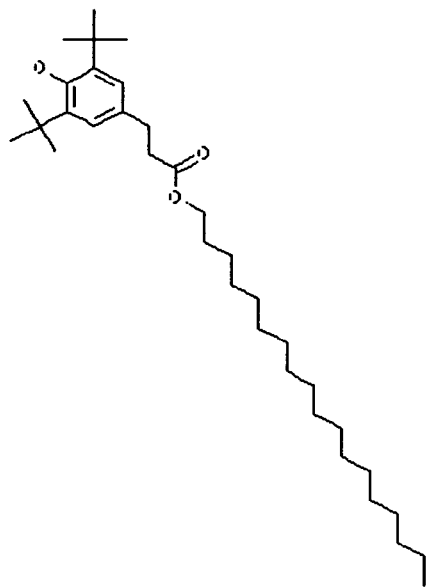
FIGS. 7A-7F depict the chemical structures of exemplars of the phenolic antioxidant proteasome inhibitors of the invention.
Figure 7B:
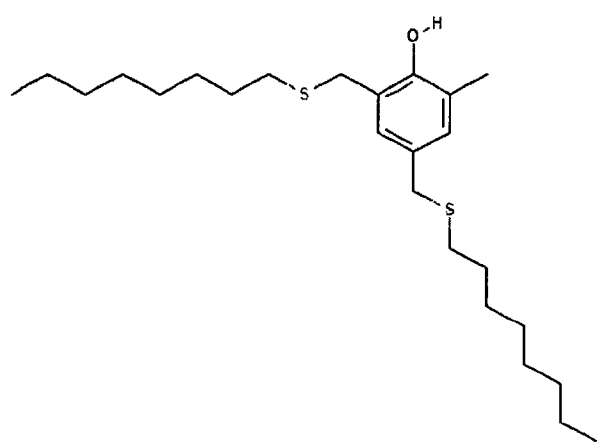
Figure 7C:
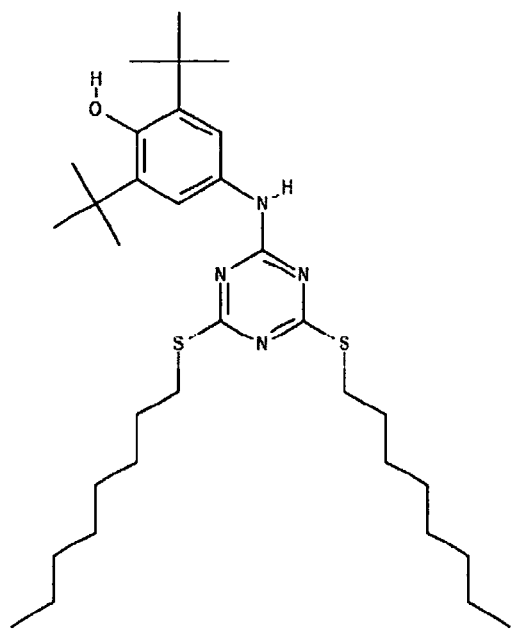
Figure 7D:
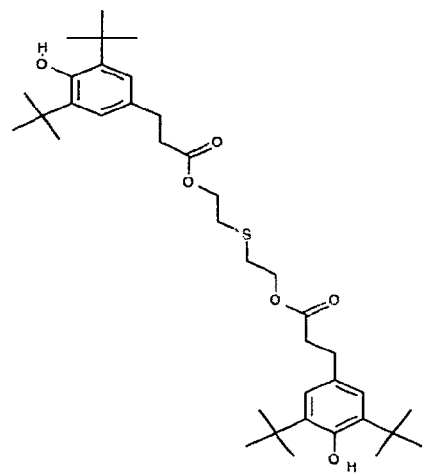
Figure 7E:
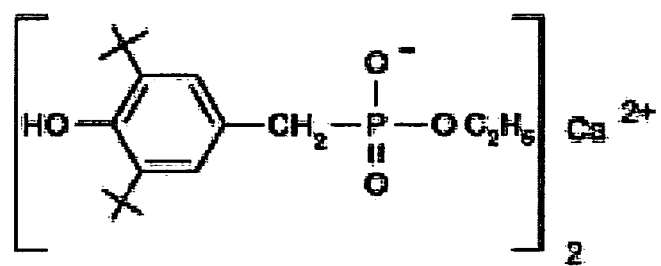
Figure 7F:
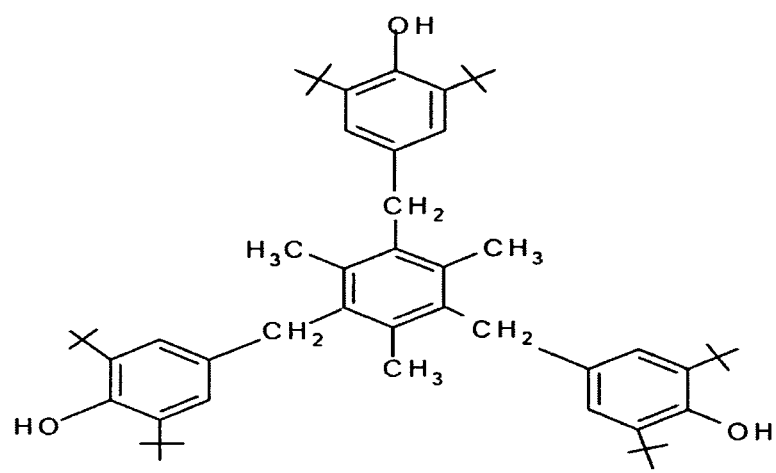

The quinic acid esters resemble the proteasome inhibitor (−)-epigallocatechin gallate [(−)-EGCG] in that they contain hydroxylated aromatic carboxylic acids esterified to a polyhydroxylated aliphatic ring (FIG. 3). Based upon this similarity, and the previous finding that epigallocatechin gallate is an inhibitor of proteasomes (Ren et al., (2000) Oncogene 19, 1419-1427; Nam et al., (2001) *J. Biol. Chem.* 276, 13322-13330)), the ability of fractions T-2, T-5, and T-6 to inhibit proteasome function was assessed. To determine the ability of quinic acid esters to inhibit proteasome activity, a fluorescent substrate activity assay was performed with purified 20S proteasome. Epigallocatechin gallate (EGCG, Sigma Chemical Company, St Louis, Mo.) was used as a positive control for proteasome inhibition. To ensure complete inhibition of the proteasome, 100 µM EGCG was used. The compound 3,5-dicaffeoylquinic acid (3,5-DCQ) was tested against proteasome activity in three different concentrations: 20, 100, and 200 μg/ml, which correspond to 37, 183, and 366 μM respectively (FIG. 4). The IC50 value for 3,5-DCQ was determined to be approximately 64 μM. In contrast, neochlorogenic acid was found to be much weaker, with the IC50 value of ~564 μM for the purified 20S proteasome (FIG. 4). The potency of fraction T6 (3,4-DCQ) was between that of 3,5-DCQ and neochlorogenic acid: at 100 μM, fractions T-5, T-6 and T-2 inhibited the proteasomal chymotrypsin-like activity by 60, 40 and 21%, respectively. These data suggest that 3,5-DCQ has the greatest proteasome-inhibitor activity in all the structurally related substances tested (FIG. 5).

Additional experiments wee conducted to investigate the role of the caffeoyl esters as useful compound to inhibit inositol-1,4,5-triphosphate 3 kinase activity. An assay was performed as described in Mayr et al., (2005) *J. Biol. Chem.* 280: 13229-13240, incorporated herein by reference. In the assay, PTTC was shown to inhibit IP-3 kinase activity as shown in FIG. 6. The cinnamate esters of the invention are likely to behave in a similar manner to inhibit IP-3 kinase activity. Inhibition of the kinase activity may be important in HIV. Thus, the compounds of the invention may be used alone, or in combination, with existing therapies for the treatment of HIV.

Example 3

Inhibition of Proteasome Activity in Jurkat T Cell Extracts by HPLC-Purified Mate Tea Fractions This example describes the how to analyze the inhibitory effect of isolated fractions of mate tea in vivo, using cell extracts of the Jurkat cancer cell line. Whole cell extracts (20 μg) of Jurkat T cells were incubated for 60 min at 37° C. with 20 μM of fluorogenic peptide substrate Suc-Leu-Leu-Val-Tyr-AMC in 100 ml of the assay buffer, with or without a mate tea fraction at indicated concentrations. The hydrolyzed AMCs were quantified as described above.

The abilities of 3,5-DCQ and neochlorogenic acid to inhibit the 26S proteasome activity in Jurkat cell extracts was tested. The results show that 3,5-DCQ at 20 μg/ml (37 μM) inhibited the proteasome activity by ~50%, and at 100 μg/ml (183 μM) inhibited the proteasome activity by ~85%, which was almost as potent as 100 μM EGCG. In this assay, neochlorogenic acid (5-CQ) was also able inhibit the proteasome activity (~30% at 20 μg/ml or 56 μM and ~75% at 100 μg/ml or 282 μM), although its potency was weaker than that of 3,5-DCQ. This data further demonstrates that 3,5-DCQ is able to inhibit the chymotrypsin-like activity of the 26S proteasome.

To investigate the inhibitory effect of the fractions on cell cycle, Jurkat cells exposed to each fraction were analyzed by flow cytometry. Cell cycle analysis based on DNA content was performed as described previously (See Nam et al., 2001). The cell cycle distribution is shown as the percentage of cells containing G1, S, G2, and M DNA judged by propidium iodide staining.

The proteasome-inhibitory potencies of 3,5-DCQ and neochlorogenic acid were identified as being associated with growth-inhibitory activity in vivo, based on treating Jurkat T cells with each compound at a concentration of 2 or 20 μg/ml for 24 h. After treatment, the cells were harvested and assayed by flow cytometry. 3,5-DCQ at 2 μg/ml produced a very slight arrest of Jurkat cells in the G2/M phase of the cell cycle, while 20 μg/ml increased the G2/M population by nearly 10%. In contrast, neochlorogenic acid at the same concentrations had no effects. This data suggests that 3,5-DCQ inhibits the proteasome in intact tumor cells, resulting in G2/M arrest.

This study of Mate tea derivatives suggests that proteasome inhibitors can be synthesized by varying the alcohol as well as producing multiple ester groups. The development of polycinnamate esters as proteasome inhibitors may lead to the development of topical and systemic proteasome inhibitors, which may be used in inflammatory and neoplastic disorders, without the side effects of topical glucocorticoids.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A method of treating a skin disorder associated with proteasome activity selected from the group consisting of angiosarcoma, hemangioendothelioma, basal cell carcinoma, squamous cell carcinoma, malignant melanoma and Kaposi's sarcoma, psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis, wherein the dihydrocinnamate compound interacts with a proteasome to inhibit proteasome activity, and wherein the inhibition of proteasome activity treats the disorder, comprising administering a topical pharmaceutical composition to a patient in need thereof comprising an effective amount of a dihydrocinnamate compound and a pharmaceutically-acceptable carrier, wherein the dihydrocinnamate compound inhibits proteasome activity, and wherein the dihydrocinnamate compound is (i)

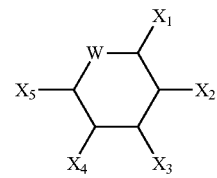

wherein W is selected from the group consisting of an alkyl group, a methylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, such that OR is a dihydrocinnamate moiety, and wherein at least one of $X_1$ to $X_5$ is said OR group;

(ii)

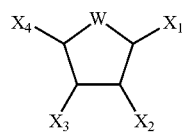

wherein W and XI-X4 are as defined above, or
(iii) a dihydrocinnamate compound selected from the group consisting of
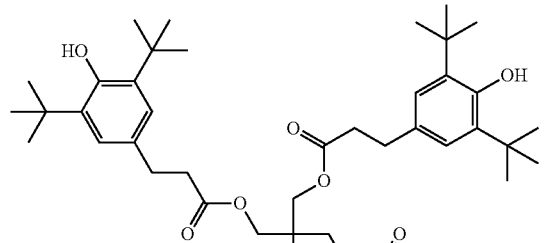
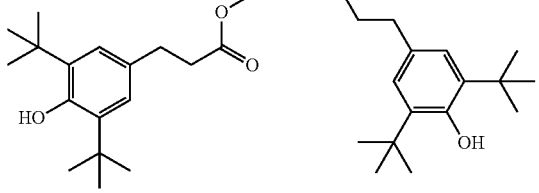
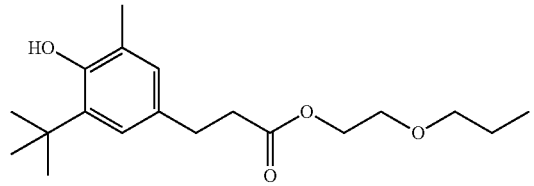
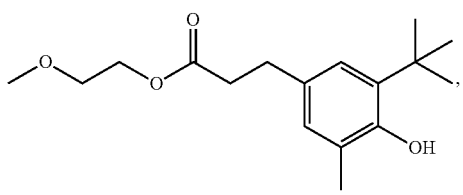
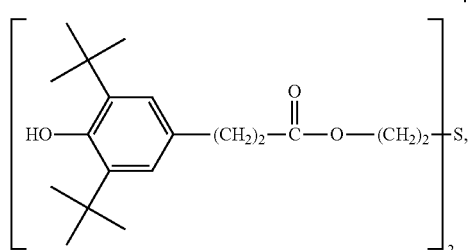
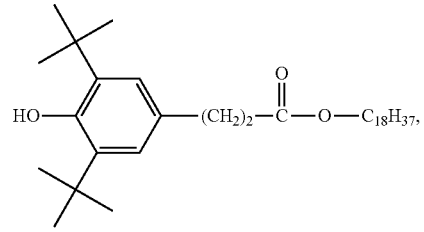
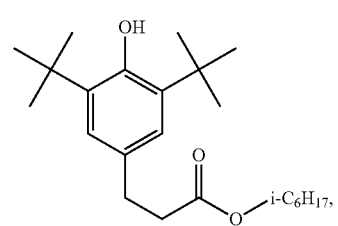
-continued
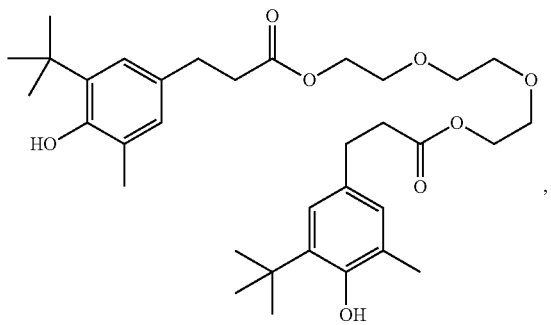,
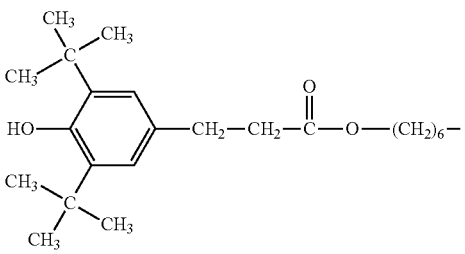
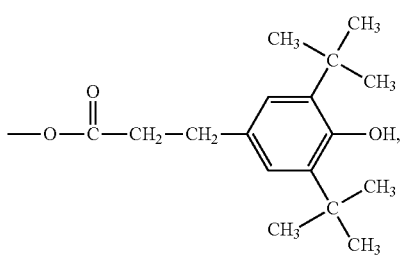,
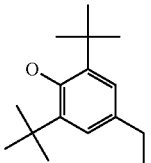
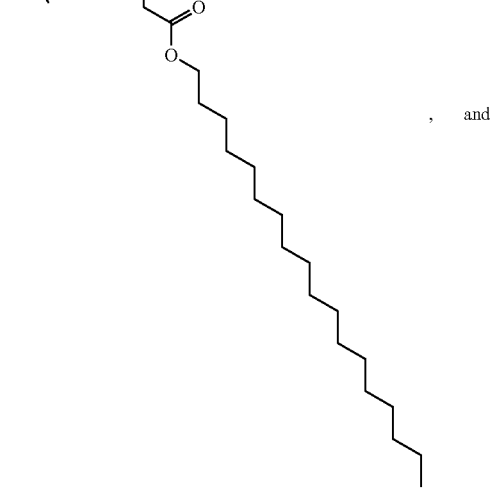, and

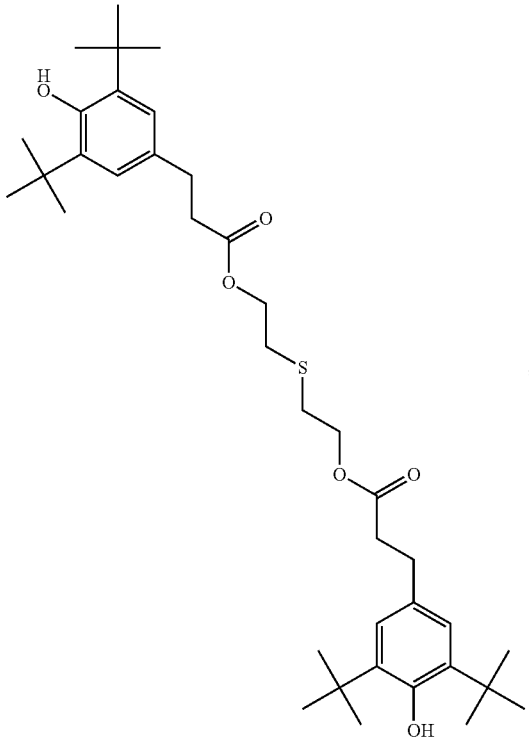

and analogs thereof wherein one or more of the hydrogen atoms on the phenyl ring in the dihydrocinnamate moiety in the listed compounds can be replaced with a moiety selected from the group consisting of halogen, hydroxyl, ether, alkyl, aryl, nitro, cyano, thiol, thioester, amino, and amido.

2. The method of claim 1, wherein the dihydrocinnamate compound inhibits a chymotrypsin-like activity of the proteasome.

3. The method of claim 1, wherein the dihydrocinnamate compound is selected from the group consisting of

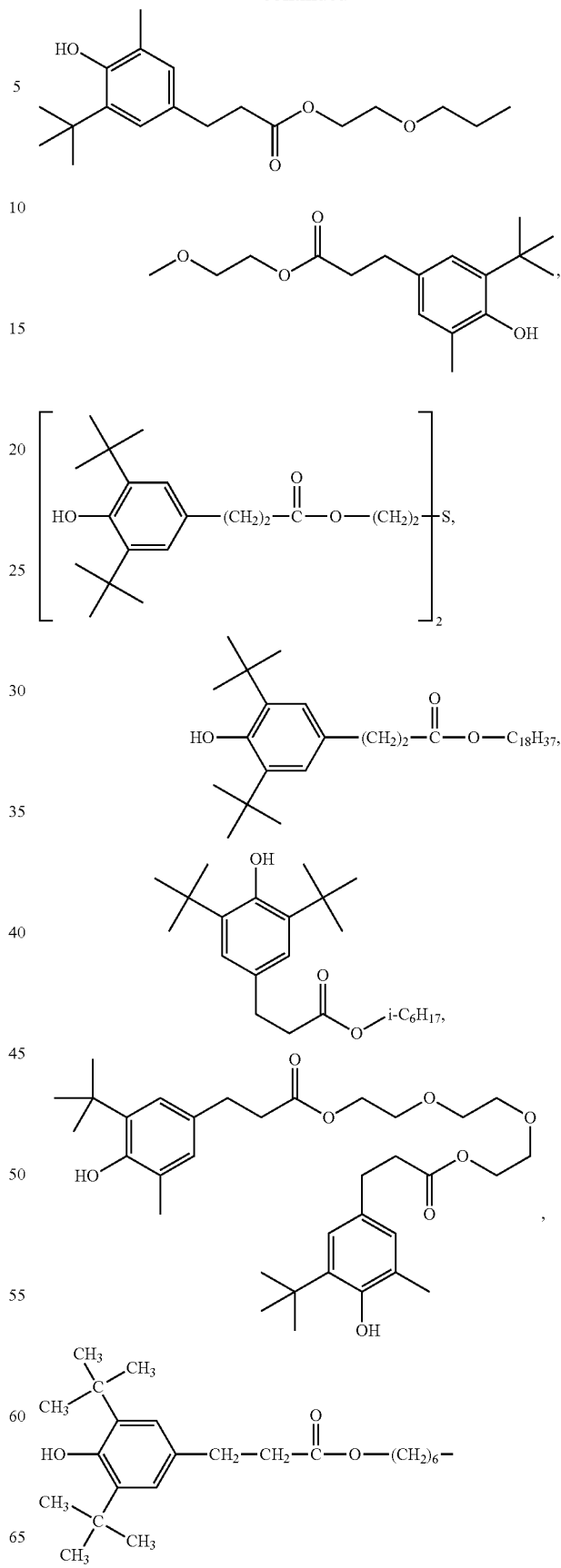

-continued

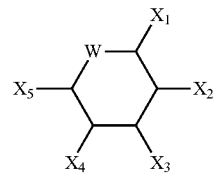

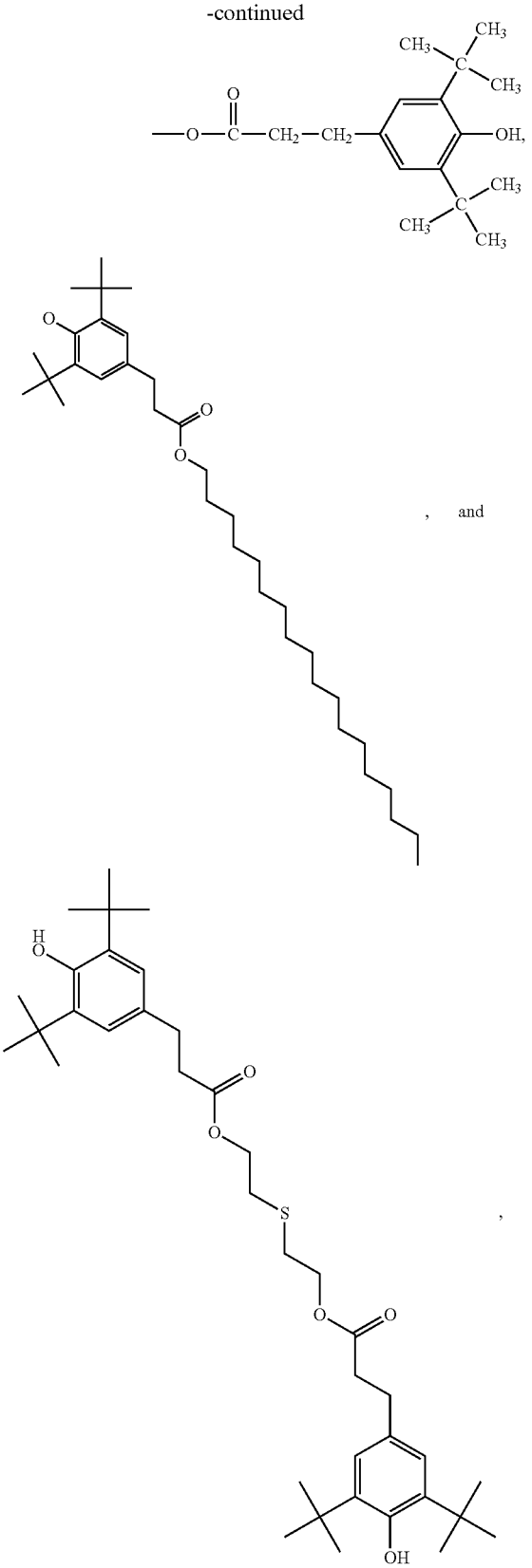, and and analogs thereof wherein one or more of the hydrogen atoms on the phenyl ring in the dihydrocinnamate moiety in the listed compounds can be replaced with a moiety selected from the group consisting of halogen, hydroxyl, ether, alkyl, aryl, nitro, cyano, thiol, thioester, amino, and amido.

4. The method of claim 1, wherein the dihydrocinnamate compound is pentaerythritol tetrakis(3,5-di-tert-butyl-4-hydroxyhydrocinnamate).

5. The method of claim 1, wherein the dihydrocinnamate compound has the formula:

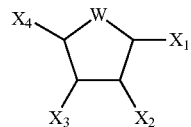

wherein W is selected from the group consisting of an alkylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, such that OR is a dihydrocinnamate moiety, and wherein at least one of $X_1$ to $X_5$ is said OR group, and analogs thereof wherein one or more of the hydrogen atoms on the phenyl ring in the moiety can be replaced with a moiety selected from the group consisting of halogen, hydroxyl, ether, alkyl, aryl, nitro, cyano, thiol, thioester, amino, and amido.

6. The method of claim 1, wherein the hydrocinnamate compound has the formula:

$$\begin{array}{c} X_4 \diagdown W \diagup X_1 \\ \mid \quad \mid \\ X_3 \quad X_2 \end{array}$$

wherein W is selected from the group consisting of an alkylene group, an amine group, an acyl group, a carbonyl group, an oxygen atom, a sulfur atom, and wherein $X_1$ to $X_4$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, such that OR is a dihydrocinnamate moiety, wherein at least one of $X_1$ to $X_4$ is said OR group, and analogs thereof wherein one or more of the hydrogen atoms on the phenyl ring in the —C(O)—CH$_2$CH$_2$-phenyl moiety can be replaced with a moiety selected from the group consisting of halogen, hydroxyl, ether, alkyl, aryl, nitro, cyano, thiol, thioester, amino, and amido, and a pharmaceutically-acceptable carrier, wherein the cinnamate compound inhibits proteasome activity.

7. A method of treating a skin disorder associated with proteasome activity selected from the group consisting of lupus, arthritis, and multiple sclerosis, wherein the dihydrocinnamate compound interacts with a proteasome to inhibit proteasome activity, and wherein the inhibition of proteasome activity treats the disorder, comprising administering a topical pharmaceutical composition to a patient in need thereof comprising an effective amount of a dihydrocinnamate compound and a pharmaceutically-acceptable carrier, wherein the dihydrocinnamate compound inhibits proteasome activity, and wherein the dihydrocinnamate compound is (i)

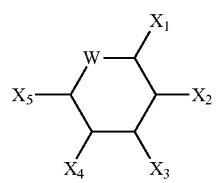

wherein W is selected from the group consisting of an alkyl group, a methylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, such that OR is a dihydrocinnamate moiety, and wherein at least one of $X_1$ to $X_5$ is said OR group;

(ii)

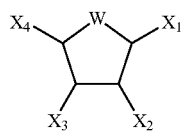

wherein W and X1-X4 are as defined above, or (iii) a dihydrocinnamate compound selected from the group consisting of

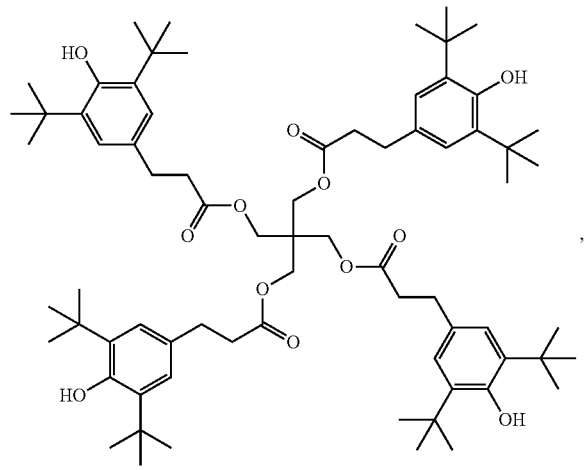

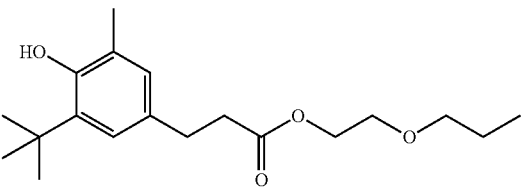

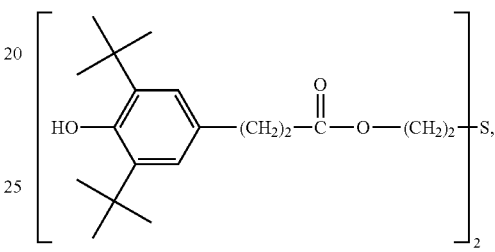

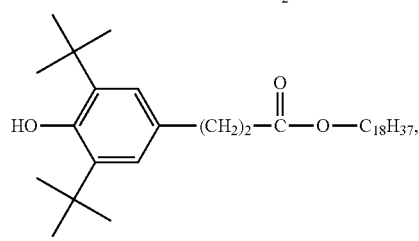

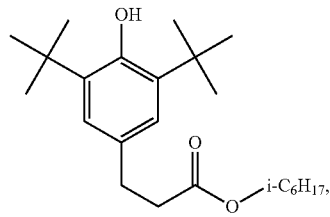

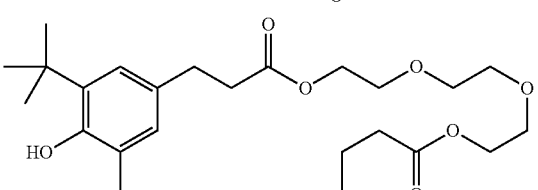

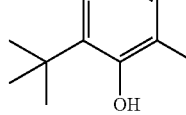

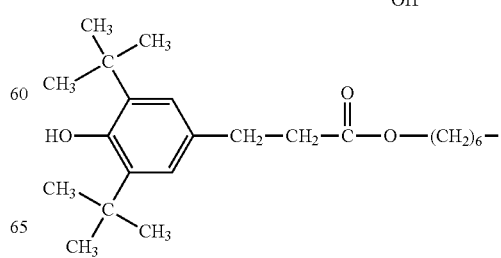

-continued

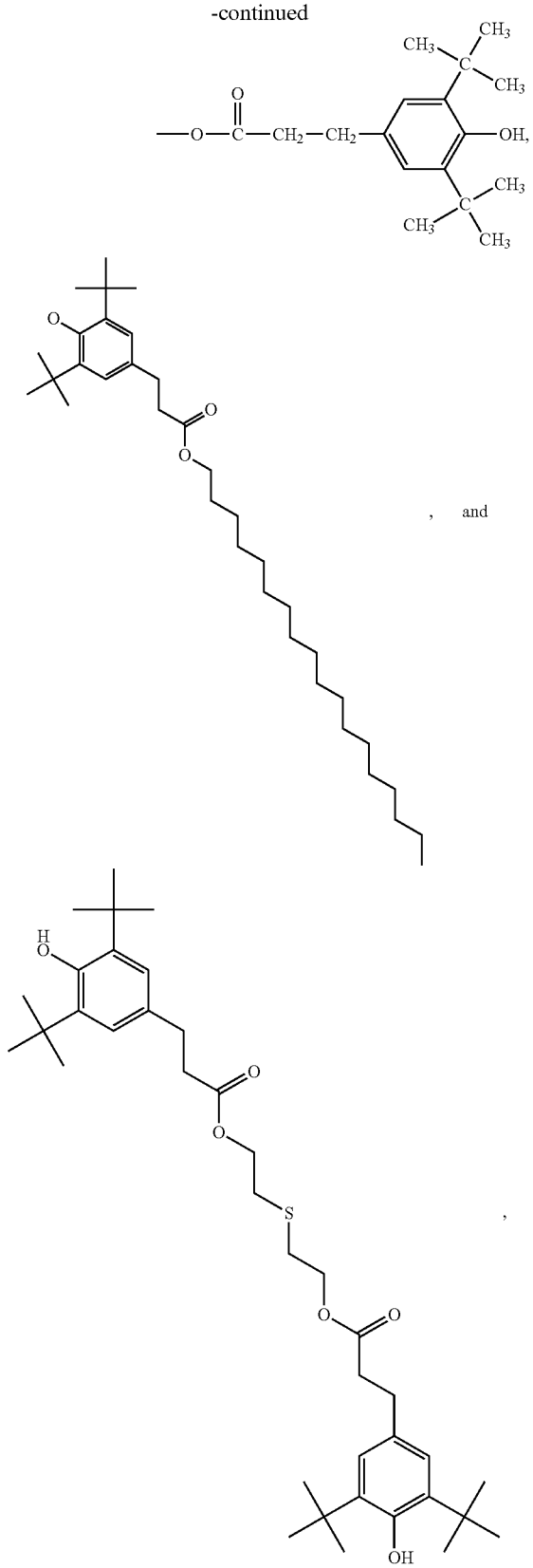

, and ety selected from the group consisting of halogen, hydroxyl, ether, alkyl, aryl, nitro, cyano, thiol, thioester, amino, and amido.

8. The method of claim 7, wherein the dihydrocinnamate compound in the composition of claim 1 is pentaerythritol tetrakis(3,5-di-tert-butyl-4-hydroxyhydrocinnamate).

9. The method of claim 1, wherein the dihydrocinnamate compound inhibits a chymotrypsin-like activity of the proteasome.

10. The method of claim 7, wherein the dihydrocinnamate compound is selected from the group consisting of

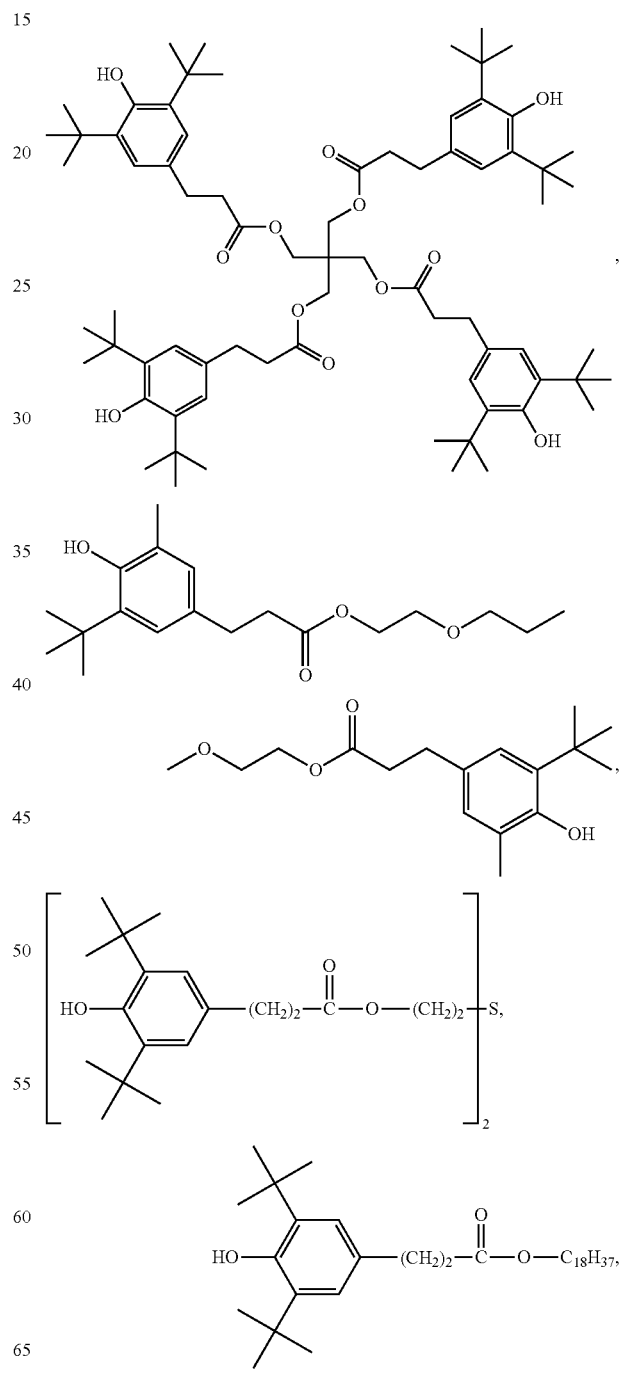

and analogs thereof wherein one or more of the hydrogen atoms on the phenyl ring in the dihydrocinnamate moiety in the listed compounds can be replaced with a moi-

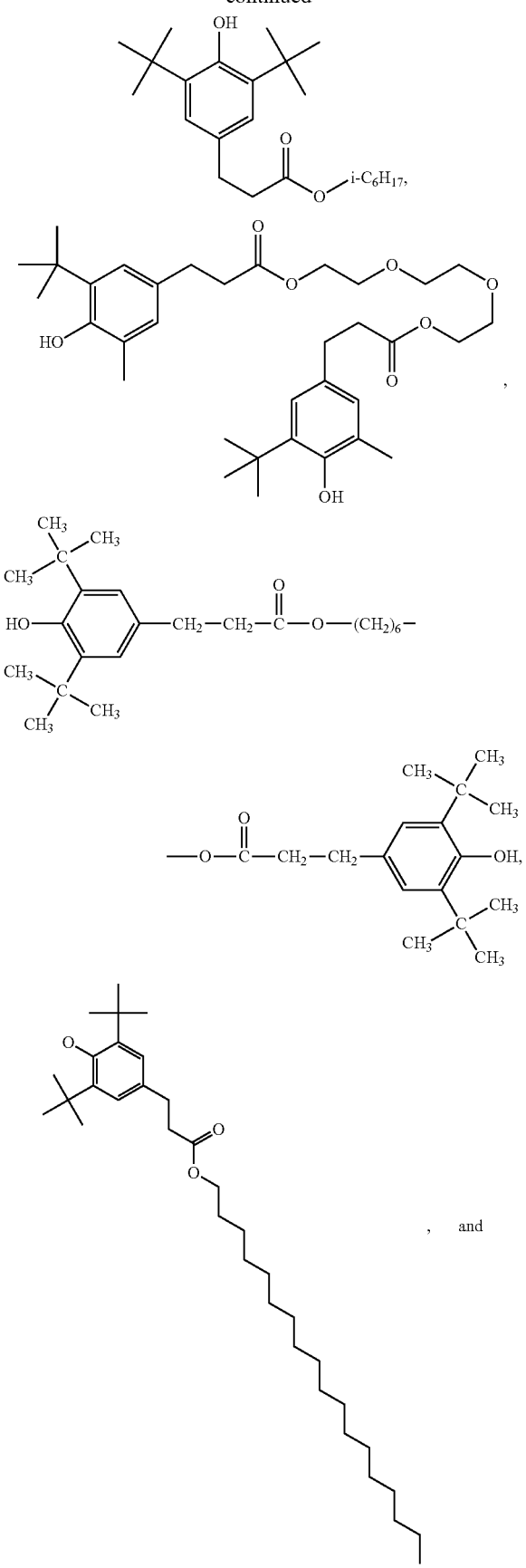

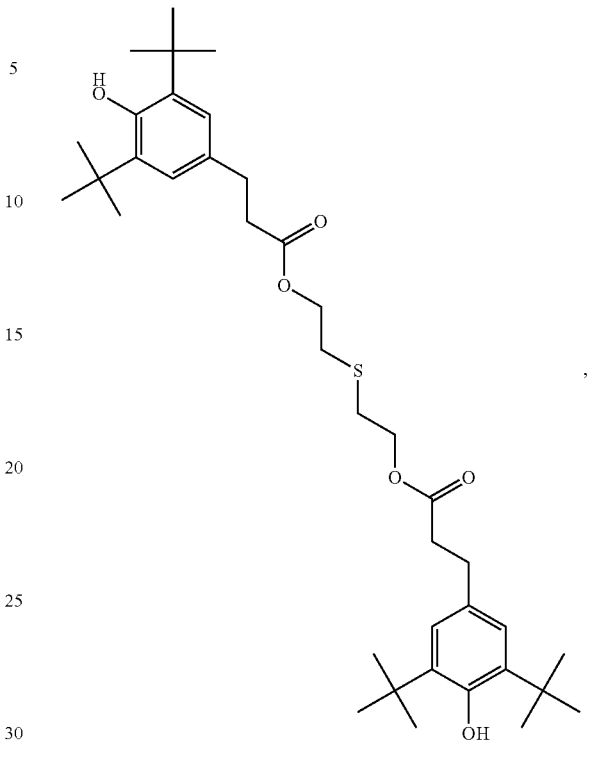

and analogs thereof wherein one or more of the hydrogen atoms on the phenyl ring in the dihydrocinnamate moiety in the listed compounds can be replaced with a moiety selected from the group consisting of halogen, hydroxyl, ether, alkyl, aryl, nitro, cyano, thiol, thioester, amino, and amido.

11. The method of claim 7, wherein the dihydrocinnamate compound is pentaerythritol tetrakis(3,5-di-tert-butyl-4-hydroxyhydrocinnamate).

12. The method of claim 7, wherein the dihydrocinnamate compound has the formula:

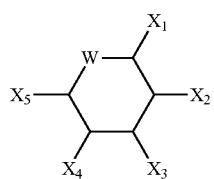

wherein W is selected from the group consisting of an alkylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, and wherein at least one of $X_1$ to $X_5$ is said OR group, and analogs thereof wherein one or more of the hydrogen atoms on the phenyl ring in the hydrocinnamate moiety can be replaced with a moiety selected from the group consisting of halogen, hydroxyl, ether, alkyl, aryl, nitro, cyano, thiol, thioester, amino, and amido.

13. The method of claim 7, wherein the dihydrocinnamate compound has the formula:

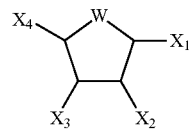

wherein W is selected from the group consisting of a methyl group, an alkyl group, a methylene group, an amine group, an acyl group, a carbonyl group, an oxygen atom, a sulfur atom, and wherein Xi to $X_4$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, wherein at least one of $X_1$ to $X_4$ is said OR group,
   and analogs thereof wherein one or more of the hydrogen atoms on the phenyl ring in the hydrocinnamate moiety can be replaced with a moiety selected from the group consisting of halogen, hydroxyl, ether, alkyl, aryl, nitro, cyano, thiol, thioester, amino, and amido,
   wherein the hydrocinnamate compound interacts with a proteasome to inhibit proteasome activity, wherein the inhibition of proteasome activity treats the disorder.

14. The method of claim 1, wherein the disorder is psoriasis.

15. The method of claim 1, wherein the disorder is acne, actinic keratosis, or rosacea.

16. A method of treating a skin disorder associated with proteasome activity selected from the group consisting of bladder cancer, leukemias, lymphomas, sarcomas, and epithelial cancers, wherein the dihydrocinnamate compound interacts with a proteasome to inhibit proteasome activity, and wherein the inhibition of proteasome activity treats the disorder, comprising administering a topical pharmaceutical composition to a patient in need thereof comprising an effective amount of a dihydrocinnamate compound and a pharmaceutically-acceptable carrier, wherein the dihydrocinnamate compound inhibits proteasome activity, and wherein the dihydrocinnamate compound is (i)

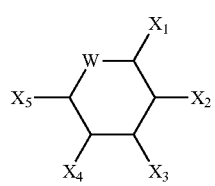

wherein W is selected from the group consisting of an alkyl group, a methylene group, an amine group, an acyl group, a carbonyl group, an oxygen atom, a sulfur atom, and wherein $X_1$ to $X_5$ are independently selected from the group consisting of a hydrogen atom, a halogen, a hydroxyl group, an ether group, a nitro group, a cyano group, a thiol group, a thioether group, an amino group, an amido group, and an OR group, where R is —C(O)—CH$_2$CH$_2$-phenyl, such that OR is a dihydrocinnamate moiety, and wherein at least one of $X_1$ to $X_5$ is said OR group;

(ii)

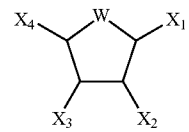

wherein W and XI-X4 are as defined above, or (iii) a dihydrocinnamate compound selected from the group consisting of

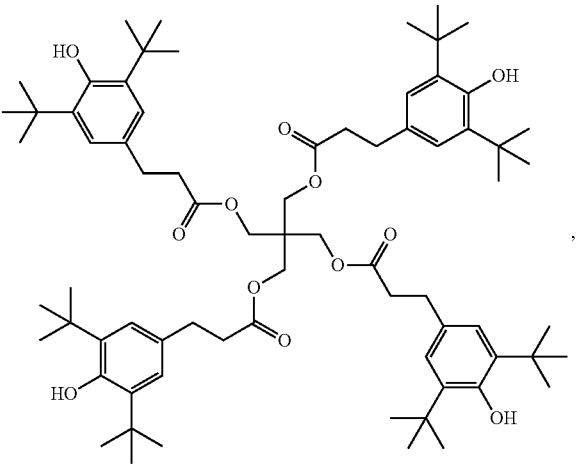

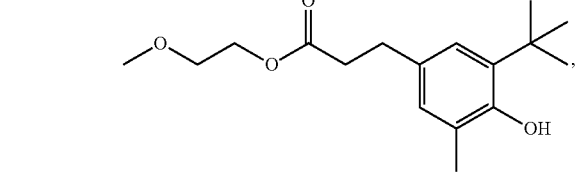

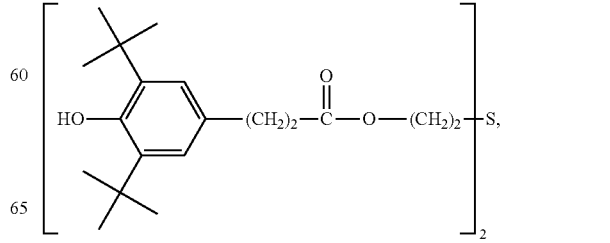

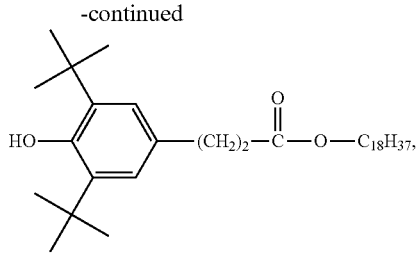

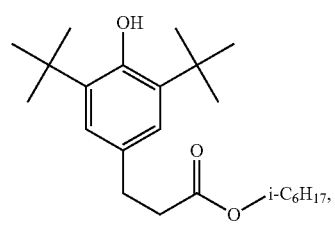

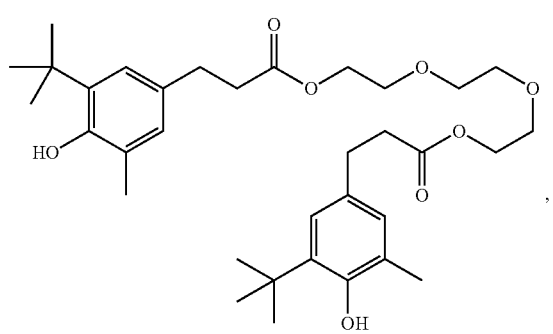

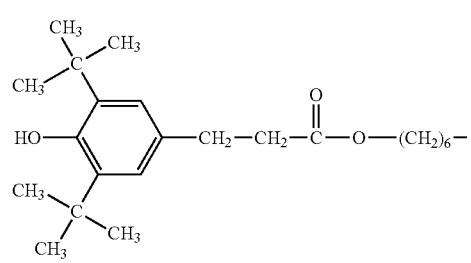

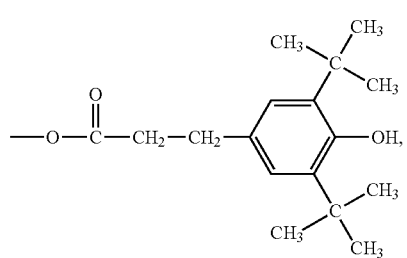

and analogs thereof wherein one or more of the hydrogen atoms on the phenyl ring in the dihydrocinnamate moiety in the listed compounds can be replaced with a moiety selected from the group consisting of halogen, hydroxyl, ether, alkyl, aryl, nitro, cyano, thiol, thioester, amino, and amido.

17. The method of claim 16, wherein the dihydrocinnamate compound is pentraerythritol tetrakis(3,5-di-tert-butyl-4-hydroxyhydrocinnamate).

* * * * *

UNITED STATES PATENT AND TRADEMARK OFFICE
CERTIFICATE OF CORRECTION

PATENT NO. : 8,809,283 B2
APPLICATION NO. : 11/437244
DATED : August 19, 2014
INVENTOR(S) : Jack L. Arbiser It is certified that error appears in the above-identified patent and that said Letters Patent is hereby corrected as shown below:

In the Specification

Column 1, Line 8, please insert the below, after the "Field of the Invention":
--"This invention was made with government support under grant AR002030 awarded by the National Institutes of Health. The government has certain rights in the invention."--

Signed and Sealed this
Twenty-seventh Day of September, 2022

*Katherine Kelly Vidal*

Katherine Kelly Vidal
*Director of the United States Patent and Trademark Office*